United States Patent
Elferri et al.

(10) Patent No.: US 8,639,324 B2
(45) Date of Patent: Jan. 28, 2014

(54) RESPIRATORY PARAMETERS FOR ARRHYTHMIA DETECTION AND THERAPY

(75) Inventors: Efdal Elferri, Blaine, MN (US); Randall L. McPherson, Minneapolis, MN (US); Donald L. Hopper, Maple Grove, MN (US); Gary T. Seim, Minneapolis, MN (US); James O. Gilkerson, Stillwater, MN (US); Dan Li, Shoreview, MN (US); David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/353,515

(22) Filed: Jan. 19, 2012

(65) Prior Publication Data

US 2012/0197323 A1 Aug. 2, 2012

Related U.S. Application Data

(60) Provisional application No. 61/438,734, filed on Feb. 2, 2011.

(51) Int. Cl.
*A61B 5/0205* (2006.01)
*A61N 1/365* (2006.01)
*A61N 1/39* (2006.01)

(52) U.S. Cl.
USPC .................................. 607/4; 607/5; 600/484

(58) Field of Classification Search
USPC .......................................... 607/4, 5; 600/484
See application file for complete search history.

(56) References Cited

U.S. PATENT DOCUMENTS

| 5,370,667 | A | | 12/1994 | Alt |
| 5,431,685 | A | | 7/1995 | Alt |
| 5,836,975 | A | | 11/1998 | DeGroot |
| 5,987,356 | A | * | 11/1999 | DeGroot ........................... 607/5 |
| 6,076,015 | A | * | 6/2000 | Hartley et al. ................... 607/20 |
| 6,370,424 | B1 | * | 4/2002 | Prutchi .......................... 600/547 |
| 6,459,929 | B1 | * | 10/2002 | Hopper et al. ................. 600/513 |
| 6,738,667 | B2 | | 5/2004 | Deno et al. |
| 7,142,919 | B2 | | 11/2006 | Hine et al. |
| 7,403,813 | B1 | * | 7/2008 | Farazi et al. ................... 600/515 |

(Continued)

FOREIGN PATENT DOCUMENTS

| WO | WO-2009136817 A1 | | 11/2009 | |
| WO | WO 2009136817 A1 | * | 11/2009 | ........... A61B 5/0464 |

OTHER PUBLICATIONS

Sears, Samuel F., et al., "Quality of Life and Psychological Functioning ICD Patients", Heart 87(5), (May 2002), 488-493.

*Primary Examiner* — Carl H Layno
*Assistant Examiner* — Erin Piateski
(74) *Attorney, Agent, or Firm* — Schwegman Lundberg Woessner, P.A.

(57) ABSTRACT

An implantable or ambulatory medical device can include a cardiac signal sensing circuit configured to provide a sensed cardiac depolarization signal of a heart of a subject, a respiration sensing circuit configured to provide a signal representative of respiration of the subject, and a control circuit communicatively coupled to the cardiac signal sensing circuit and the respiration circuit. The control circuit includes a tachyarrhythmia detection circuit configured to determine heart rate using the depolarization signal, determine a respiration parameter of the subject using the respiration signal, calculate a ratio using the determined heart rate and the determined respiration parameter, generate an indication of tachyarrhythmia when the calculated ratio satisfies a specified detection ratio threshold value, and provide the indication of tachyarrhythmia to a user or process.

11 Claims, 6 Drawing Sheets

(56) References Cited

U.S. PATENT DOCUMENTS

| | | |
|---|---|---|
| 7,558,627 B1 | 7/2009 | Turcott |
| 2003/0105491 A1* | 6/2003 | Gilkerson et al. ............ 607/5 |
| 2005/0154421 A1* | 7/2005 | Ousdigian ................. 607/14 |
| 2006/0195147 A1* | 8/2006 | Gilkerson et al. ............ 607/5 |
| 2007/0135848 A1* | 6/2007 | Kim et al. ................. 607/5 |
| 2008/0275349 A1* | 11/2008 | Halperin et al. ........... 600/484 |
| 2009/0163966 A1* | 6/2009 | Perschbacher et al. ........ 607/4 |
| 2009/0234240 A1* | 9/2009 | Kuenzler et al. ........... 600/529 |
| 2010/0030293 A1* | 2/2010 | Sarkar et al. .............. 607/18 |

\* cited by examiner

US 8,639,324 B2

RESPIRATORY PARAMETERS FOR ARRHYTHMIA DETECTION AND THERAPY

CROSS-REFERENCE TO RELATED APPLICATION

This application claims the benefit of priority of U.S. Provisional Application No. 61/438,734, filed on Feb. 2, 2011, under 35 U.S.C. §119(e), which is hereby incorporated by reference in its entirety.

BACKGROUND

Cardioverter defibrillators are medical devices that deliver an electrical shock to the heart via electrodes to terminate arrhythmias. The devices may use the same or a different set of electrodes to monitor electrical heart activity within a patient.

Automated external defibrillators (AEDs) include surface electrodes that are applied to a patient by a paramedic or other trained personnel. Wearable cardioverter defibrillators (WCDs) are personal external monitors that are worn by the patient and contain surface electrodes. The surface electrodes are arranged to provide one or both of monitoring surface electrocardiograms (ECGs) and delivering cardioverter and defibrillator shock therapy.

Implantable cardioverter defibrillators (ICDs) include implantable electrodes. The electrodes are connected to sense amplifiers to provide internal monitoring of a patient's condition. ICDs may include one or more sensors to monitor one or more other internal patient parameters. In other examples, the ICDs are included in a cardiac function management device (CFM) that provides a combination of device capabilities such as pacemaker therapy and cardiac resynchronization therapy (CRT).

Additionally, some medical devices detect events by monitoring electrical heart activity signals. These events can include heart chamber electrical depolarization and the subsequent expansions and contractions. By monitoring cardiac signals indicative of expansions or contractions, medical devices can detect abnormally rapid heart rate, such as tachyarrhythmia. Tachyarrhythmia includes ventricular tachycardia (VT) which originates from the ventricles. Tachyarrhythmia also includes rapid and irregular heart rate, or fibrillation, including ventricular fibrillation (VF). Abnormally rapid heart rate can also be due to supraventricular tachycardia (SVT). SVT is less dangerous to the patient than VT or VF. SVT includes arrhythmias such as atrial tachycardia, atrial flutter, and atrial fibrillation. A rapid heart rate can also be due to sinus tachycardia, which is a normal response to, for example, exercise or an elevated emotional state.

Typically, cardioverter defibrillators detect tachyarrhythmia by first detecting a rapid heart rate. When detected, a tachyarrhythmia can be terminated using cardioversion or defibrillation shock therapy. Other detection methods in addition to fast rate detection are used to reduce the incidence of inappropriate shocks. It is important for cardioverter defibrillators to quickly and accurately classify sensed rhythms or arrhythmias and deliver the appropriate therapy.

An example of a defibrillator with the capability to distinguish pathologic tachycardia from physiologic tachycardia by the application of a predetermined distinction criteria can be found in Alt, "Implantable Medical Interventional Device with Criteria Modification to Enhance Recognition of Tachycardia," U.S. Pat. No. 5,431,685, filed Jul. 29, 1994. An example of an implantable medical intervention device having an evaluation system to be applied against an ECG signal to recognize pathological tachycardia and distinguish it from physiological tachycardia can be found in Alt, "Device and Method for Automatically Adjusting Tachycardia Recognition Criteria based on Detected Parameter," U.S. Pat. No. 5,370,667, filed Jul. 20, 1992.

OVERVIEW

This document relates generally to systems, devices, and methods for classifying cardiac rhythms. An example of an implantable or ambulatory medical device can include a cardiac signal sensing circuit configured to provide a sensed cardiac depolarization signal of a heart of a subject, a respiration sensing circuit configured to provide a signal representative of respiration of the subject, and a control circuit communicatively coupled to the cardiac signal sensing circuit and the respiration circuit. The control circuit includes a tachyarrhythmia detection circuit configured to determine heart rate using the depolarization signal, determine a respiration parameter of the subject using the respiration signal, calculate a ratio using the determined heart rate and the determined respiration parameter, generate an indication of tachyarrhythmia when the calculated ratio satisfies a specified detection ratio threshold value, and provide the indication of tachyarrhythmia to a user or process.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

A medical device may include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable, partially implantable, wearable, or other ambulatory device need not include all of the features described herein, but may be implemented to include selected features that provide for unique structures or functionality. Such a device may be implemented to provide a variety of therapeutic or diagnostic functions.

This document discusses systems and methods for improved detection of tachyarrhythmia for a patient or subject. A rapid and unstable heart rate associated with tachyarrhythmia can prevent the heart chambers from filling properly; resulting in a drop in a patient's blood pressure. Sometimes, a heart rate becomes rapid but a patient's hemodynamic system remains stable, i.e. the heart rate is regular enough so that the heart chambers are able to fill adequately to maintain adequate blood pressure. A proper assessment of hemodynamic system stability is useful in making a decision in whether to deliver or to delay treatment.

Figure 1:
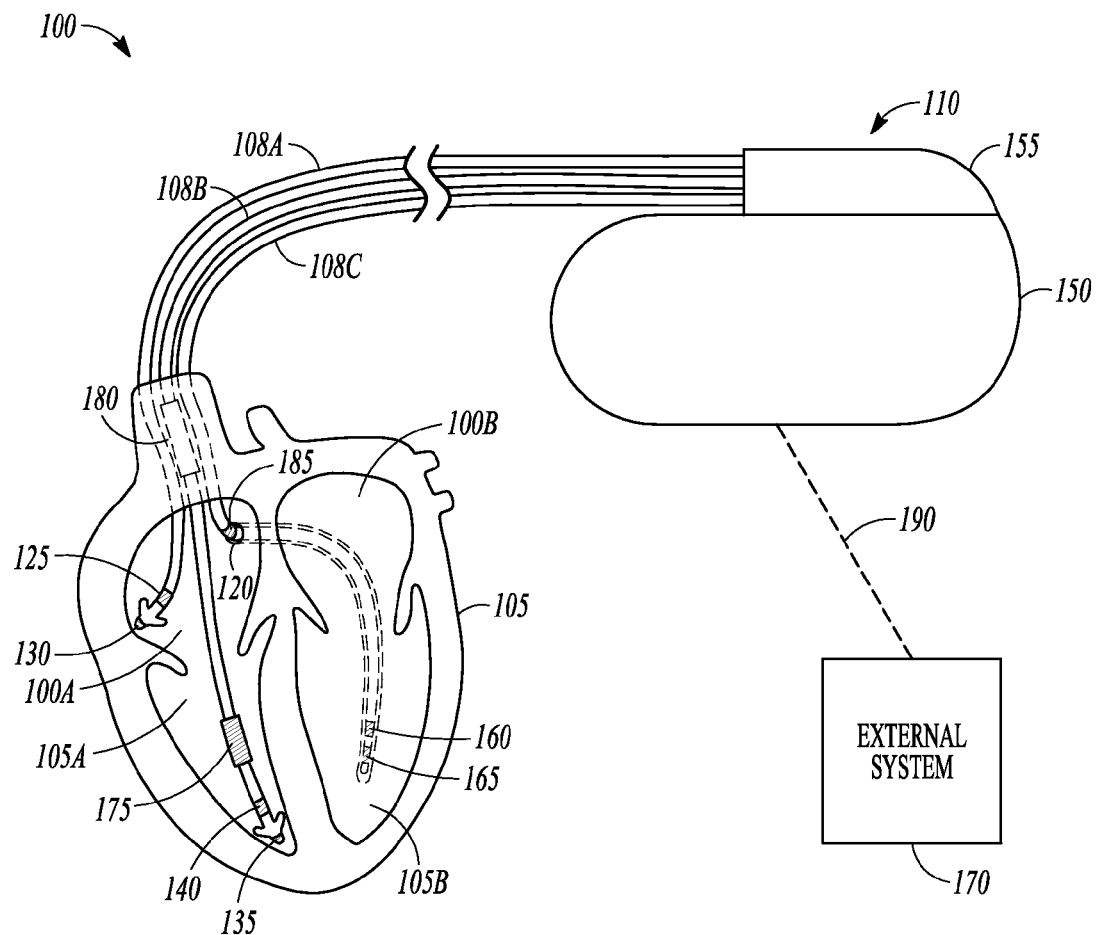
FIG. 1 is an illustration of portions of a system that uses an IMD.

Ambulatory medical devices include medical devices that can be worn, implanted, or partially implanted. FIG. 1 is an illustration of portions of a system that uses an implantable medical device (IMD) 110. Examples of IMD 110 include, without limitation, a cardioverter defibrillator, a pacer, a cardiac resynchronization therapy (CRT) device, or a combination of such devices. The system also typically includes an IMD programmer or other external device 170 that communicates wireless signals 190 with the IMD 110, such as by using radio frequency (RF) or other telemetry signals.

The IMD 110 is coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies, voltages, and currents involved in defibrillation.

The IMD 110 may include a third cardiac lead 108C attached to the IMD 110 through the header 155. The third cardiac lead 108C includes ring electrodes 160 and 165 placed in a coronary vein lying epicardially on the left ventricle (LV) 105B via the coronary vein. The third cardiac lead 108C may include a ring electrode 185 positioned near the coronary sinus (CS) 120. Lead 108C optionally provides resynchronization therapy to the heart 105. Resynchronization therapy is typically delivered to the ventricles in order to better synchronize the timing of depolarizations between ventricles.

Lead 108B may include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150.

Note that although a specific arrangement of leads and electrodes are shown the illustration, the present methods and systems will work in a variety of configurations and with a variety of electrodes. Other forms of electrodes include meshes and patches which may be applied to portions of heart 105 or which may be implanted in other areas of the body to help "steer" electrical currents produced by IMD 110. The IMDs may be configured with a variety of electrode arrangements, including transvenous, endocardial, or epicardial electrodes (e.g., intrathoracic electrodes), or subcutaneous, non-intrathoracic electrodes, such as can, header, or indifferent electrodes, or subcutaneous array or lead electrodes (e.g., non-intrathoracic electrodes). WCDs and AEDs may contain surface electrode arrangements for one or both of monitoring surface electrocardiograms (ECGs) and delivering cardioverter and defibrillator shock therapy. Implantable electrode arrangements using electrodes implanted in or near a heart chamber provide for monitoring internal electrograms.

Electrograms may be sensed using electrodes to deliver electrical pacing therapy. The arrangement of such electrodes is sometimes called a rate channel (e.g., electrodes 140 and 135 in FIG. 1). Electrograms may also be sensed using electrodes to deliver higher energy shock therapy such as cardioversion or defibrillation shock therapy. This arrangement of electrodes sometimes called a shock channel (e.g., electrode 180 and an electrode formed on IMD can 150). ECGs can be sensed by a wearable device using electrodes to sense cardiac activity (rate channel), or by electrodes to deliver shock therapy (shock channel). Monitoring of electrical signals related to cardiac activity may provide early, if not immediate, diagnosis of cardiac disease.

Figure 2:
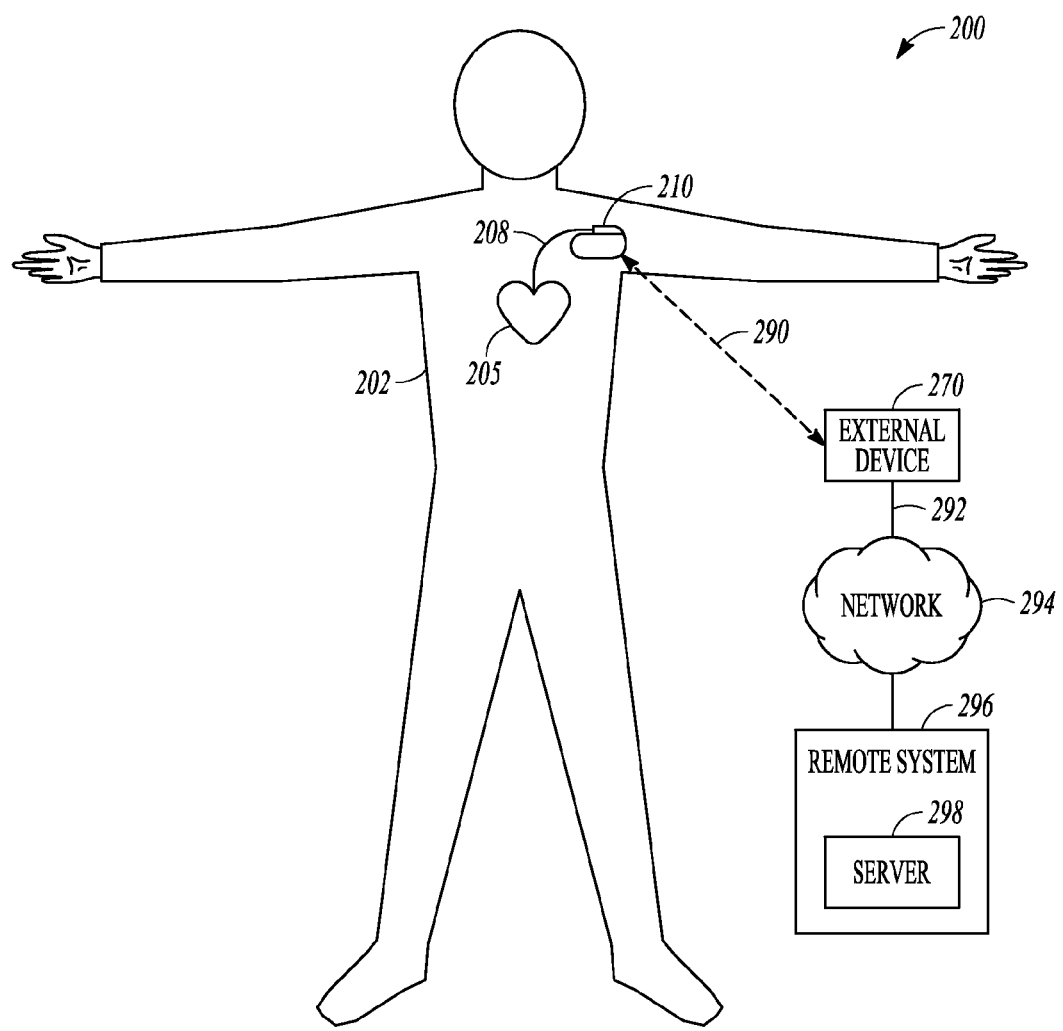
FIG. 2 is an illustration of an example of portions of another system that uses an IMD or other ambulatory medical device.

FIG. 2 is an illustration of an example of portions of another system 200 that uses an IMD or other ambulatory medical device 210 to provide a therapy to a patient 202. The system 200 typically includes an external device 270 that communicates with a remote system 296 via a network 294. The network 294 can be a communication network such as a phone network or a computer network (e.g., the internet). In some examples, the external device includes a repeater and communicated via the network using a link 292 that can be wired or wireless. In some examples, the remote system 296 provides patient management functions and can include one or more servers 298 to perform the functions.

Measurable parameters related to a patient's hemodynamic status, such as blood pressure, may remain adequate during a stable tachyarrhythmia but may become inadequately low during an unstable tachyarrhythmia. Making information related to a patient's hemodynamic status available to a medical device improves the chances that the device will make a proper assessment of heart rhythm stability. Respiration of a patient can change during a pathological arrhythmia and can correlate with changes in hemodynamic status of the subject. A minute ventilation (MV) sensor can accurately sense respiration, tidal volume, and minute ventilation. A proper assessment of patient condition makes it possible to delay the onset of treatment of a stable tachyarrhythmia or to extend the time to attempt to resolve the episode with ATP before resorting to high-energy shock therapy. This ensures that a high-energy cardioversion or defibrillation shock stimulus will convert the abnormal rhythm if the rhythm fails to convert spontaneously or fails to convert after ATP.

Figure 3:
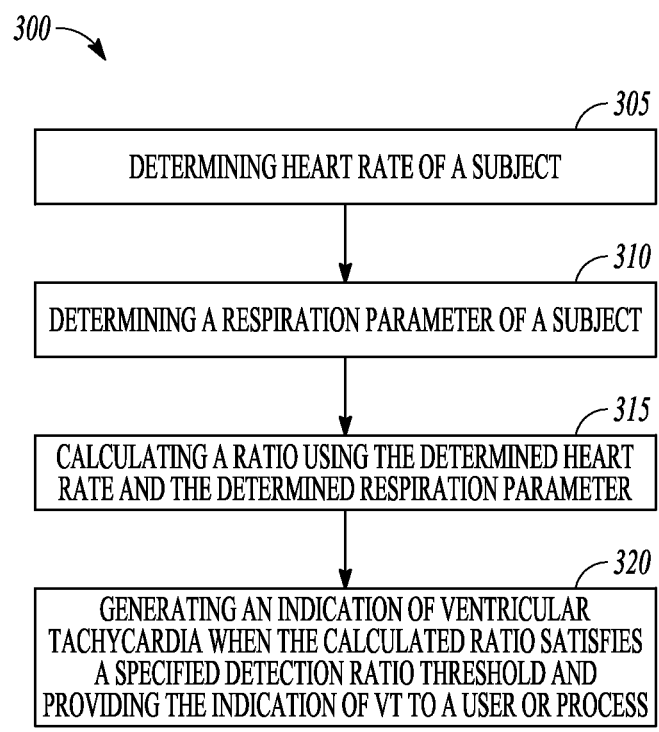
FIG. 3 shows a flow diagram of an example of a method of operating an ambulatory or implantable medical device.

FIG. 3 shows a flow diagram of an example of a method 300 of operating an implantable or other ambulatory medical device. At block 305, heart rate (HR) of a subject is determined. In some examples, the device is implantable and a cardiac signal is sensed using a cardiac signal sensing circuit electrically connected to implantable electrodes, such as tip and ring electrodes 135, 140 in FIG. 1. Heart rate can be determined from depolarizations identified in the sensed cardiac signal.

At block 310, a respiration parameter of the subject is determined. In some examples, the parameter is extracted (e.g., measured or otherwise derived) from a respiration signal sensed using a respiration sensor. The respiration signal includes respiration information of the subject. The respiration parameter can include, among other things, a measure of MV, respiration rate (RR), or tidal volume (TV).

At block 315, a ratio is calculated using the determined heart rate and the determined respiration parameter (e.g., HR/MV). At block 320, an indication of tachyarrhythmia is generated when the calculated ratio satisfies a specified tachyarrhythmia detection ratio threshold value and the indication of tachyarrhythmia is provided to a user or process.

Figure 4:
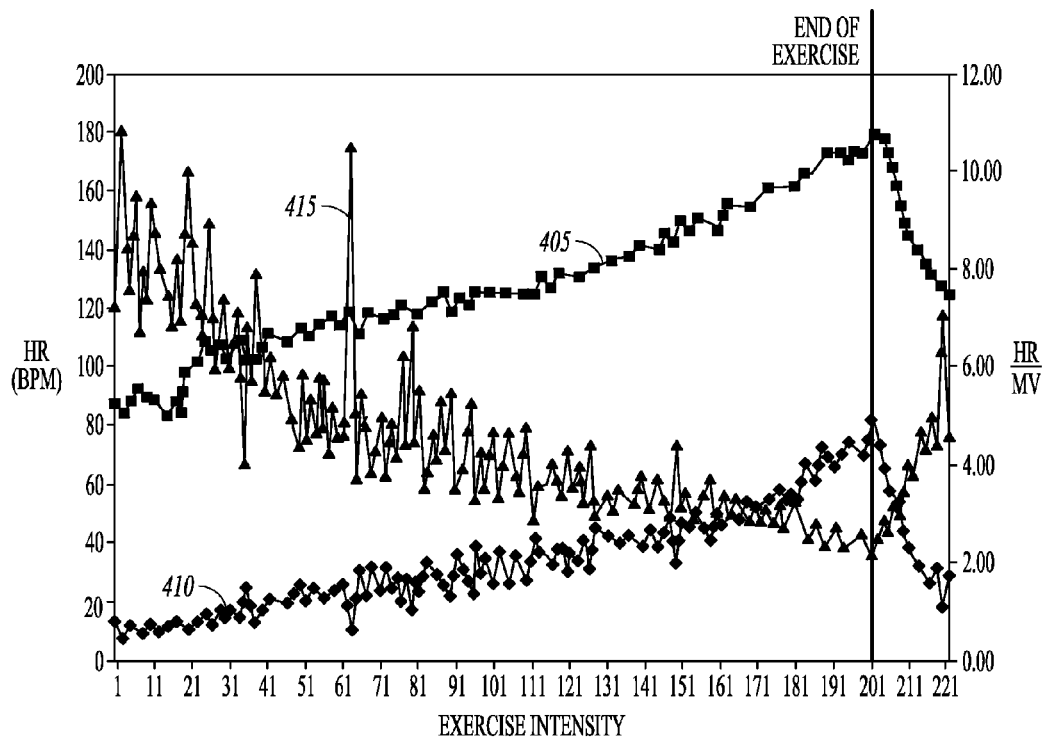
FIG. 4 shows an example of graphs of HR, MV, and the ratio of HR/MV as exercise intensity is varied.

FIG. 4 shows an example of graphs of HR 405, MV 410, and the ratio of HR/MV 415 as exercise intensity is varied. The graphs show that HR and MV increase with exercise intensity until the end of exercise. Graph 415 also shows that the ratio of HR/MV decreases as exercise intensity increases.

Figure 5:
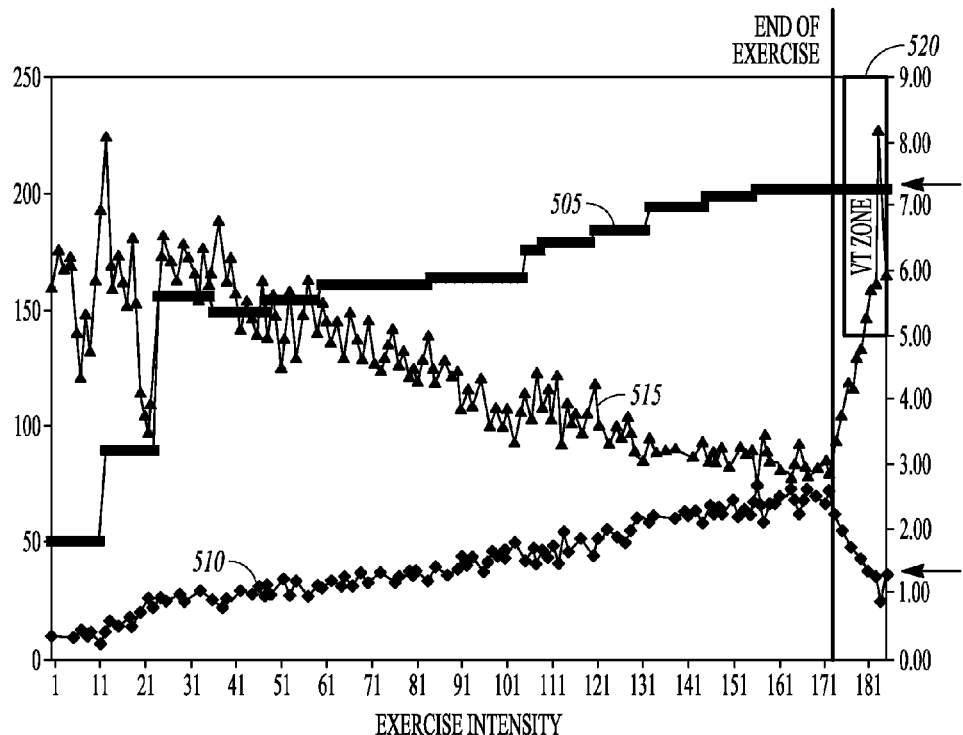
FIG. 5 shows another example of graphs of HR, MV, and the ratio of HR/MV as exercise intensity is varied.

FIG. 5 shows graphs of examples of HR 505, MV 510, and the ratio of HR/MV 515 as exercise intensity is varied. At a certain point in the exercise, the intensity of the exercise induced VT and the exercise was ended. When the exercise-induced VT occurred, the value of the ratio increased to a value much higher than the value that occurred without VT (e.g., an order of magnitude higher). A VT detection zone 520 can be specified (e.g., programmed into the device) for the ratio. When values of the ratio occur in this zone, an indication of VT or other tachyarrhythmia can be generated.

Figure 6:
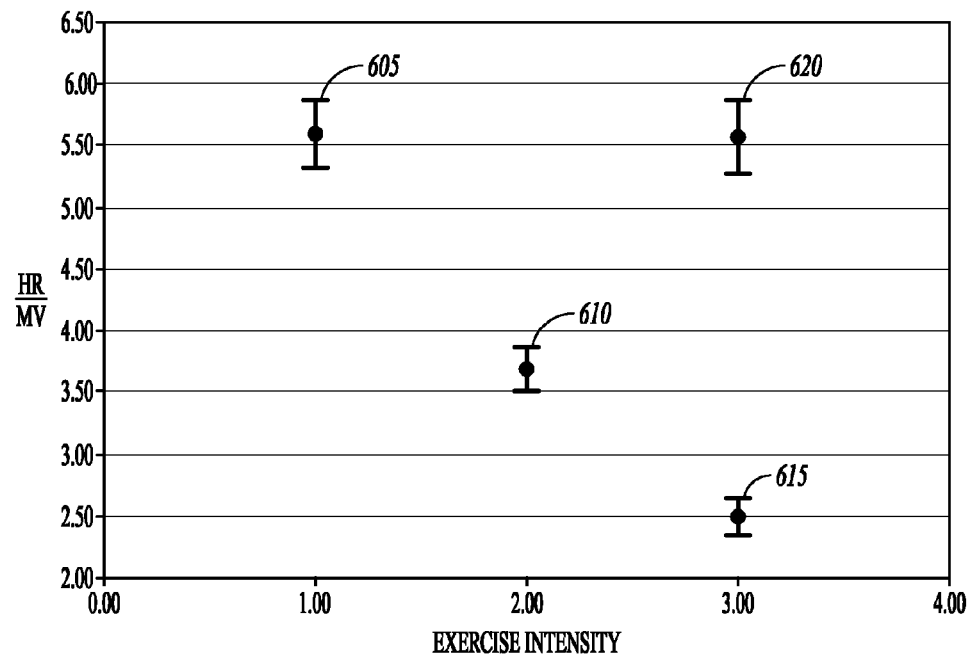
FIG. 6 shows examples values of the mean and standard error of the mean for HR/MV during levels of exercise.

FIG. 6 shows examples values of the mean and standard error of the mean for HR/MV during a low level of exercise 605, a moderate level of exercise 610, and peak exercise 615. Also shown, is the mean and standard error of the mean for HR/MV during an episode of tachyarrhythmia 620. The difference in the normal values of HR/MV and the value during tachyarrhythmia is evident in the Figure.

Figure 7:
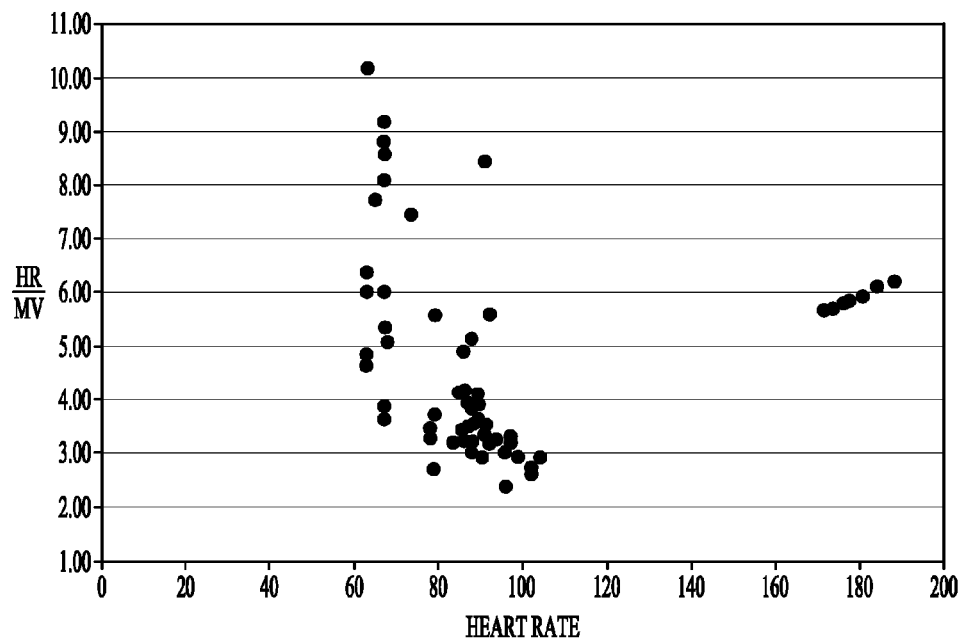
FIG. 7 is a graph showing values of HR/MV during an episode of exercise-induced VT.

FIG. 7 is a graph showing values of HR/MV during an episode of exercise-induced VT. The values of the ratio during an episode of tachyarrhythmia are outlier values and are easily distinguished from values calculated for normal physiologic activity.

Figure 8:
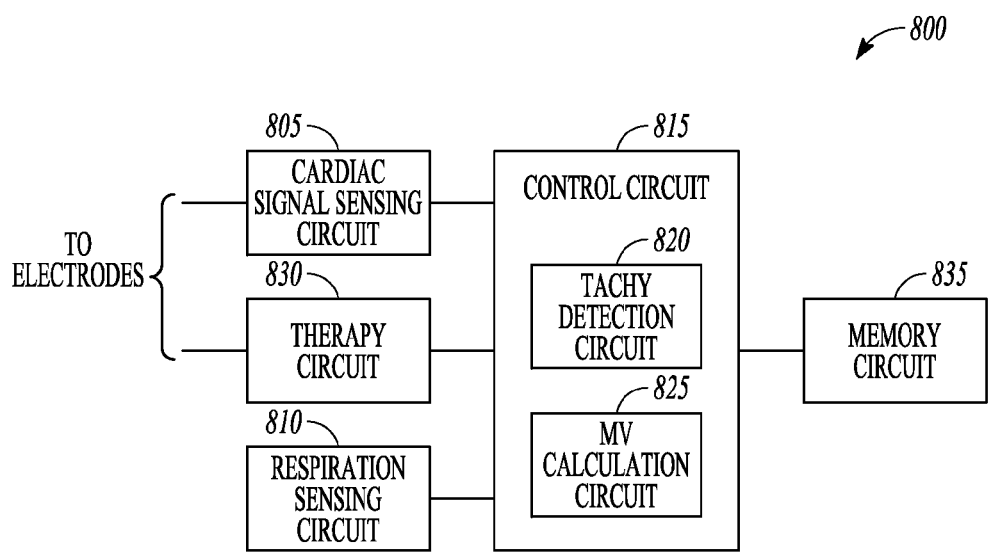
FIG. 8 is a block diagram of portions of an example of an implantable or other ambulatory medical device.

FIG. 8 is a block diagram of portions of an example of an implantable or other ambulatory (e.g., wearable) medical device 800. The device 800 includes a cardiac signal sensing circuit 805 and a respiration sensing circuit 810. The cardiac signal sensing circuit 805 provides a sensed cardiac depolarization signal of a heart of a subject. The respiration sensing circuit 810 provides a sensed signal representative of respiration of the subject. This respiration signal can be indicative of inspiratory volume or flow, expiratory volume or flow, breath rate or timing, or any combination, permutation, or component of the respiration of the subject.

In some examples, the device 800 is implantable. The cardiac signal sensing circuit 805 can include one or more sense amplifiers that are electrically connectable to implantable electrodes (e.g., one or more of the electrodes shown in the arrangement of FIG. 1) to sense cardiac depolarization in the right ventricle or left ventricle. Such electrodes can be used for monitoring heart rate. The respiration sensing circuit 810 can include an impedance sensing circuit, such as an intra-thoracic impedance sensing circuit that provides an intra-thoracic impedance signal. The intra-thoracic impedance signal can be sensed across the thorax region of the subject and includes respiration information.

To measure a region's impedance, a medical device provides current between cardiac electrodes and measures the resulting voltage using the same or different electrodes. The impedance can be determined by the medical device using Ohm's Law (R=V/I). For instance, intra-thoracic impedance can be sensed between ring electrode 140 and an electrode formed on the IMD can 150. An approach to measuring thoracic impedance is described in Hartley et al., U.S. Pat. No. 6,076,015 "Rate Adaptive Cardiac Rhythm Management Device Using Transthoracic Impedance," filed Feb. 27, 1998, which is incorporated herein by reference in its entirety.

In some examples, the device 800 is wearable. The cardiac signal sensing circuit 805 can include surface electrodes to sense the cardiac signal (e.g., an electrocardiogram or ECG). In some examples, the respiration sensing circuit 810 can include an accelerometer. The accelerometer can produce an acceleration signal that is representative of motion of the thorax region of the subject. The respiration signal can be extracted from the acceleration signal (e.g., by signal filtering). In some examples, the respiration sensing circuit 810 includes one or more of a volume or flow sensor, and a pressure sensor.

The device 800 includes a control circuit 815 communicatively coupled to the cardiac signal sensing circuit 805 and the respiration sensing circuit 810. The communicative coupling allows electrical signals to be communicated between the sensing circuits and the control circuit 815 even though there may be one or more intervening circuits between the sensing circuits and the controller circuit 815. For example, the device 800 may include a sampling circuit (not shown) integral to the control circuit 815 or electrically coupled between the sensing circuits and the control circuit 815. The sampling circuit can be configured to sample the sensed cardiac depolarization signal and respiration signal to produce cardiac depolarization data and respiration data.

The control circuit 815 can be a microprocessor, a digital signal processor, application specific integrated circuit (ASIC), microprocessor, or other type of processor, interpreting or executing instructions in software modules or firmware modules. The control circuit 815 can include other circuits or sub-circuits to perform the functions described. These circuits may include software, hardware, firmware or any combination thereof. Multiple functions can be performed in one or more of the circuits as desired.

The control circuit 815 includes a tachyarrhythmia detection circuit 820 that can determine heart rate using the cardiac depolarization signal and determine a respiration parameter of the subject using the respiration signal. The tachyarrhythmia detection circuit 820 calculates a ratio using the determined heart rate and the determined respiration parameter, and generates an indication of tachyarrhythmia when the calculated ratio satisfies a specified detection ratio threshold value.

In some examples, the tachyarrhythmia detection circuit 820 includes a minute ventilation (MV) circuit 825 configured to determine MV from the respiration signal as the respiration parameter. In certain examples, the respiration signal may be a measured impedance signal. The MV circuit 825 may extract respiration rate from the respiration signal and determine tidal volume from the measured impedance values of the respiration signal. Minute ventilation can then be calculated using the respiration rate and tidal volume as MV=RR×TV.

In some examples, the respiration signal is extracted from an acceleration signal. In some examples, the respiration signal is a pressure signal provided by a pressure sensor. In some examples the respiration signal is provided by a volume or flow sensor. Respiration rate and tidal volume are determined using one or more of the signals provided by the sensors and used to determine MV.

The tachyarrhythmia detection circuit 820 calculates a ratio of heart rate to minute ventilation (HR/MV) and generates an indication of tachyarrhythmia when the calculated HR/MV exceeds a specified tachyarrhythmia detection threshold HR/MV value. In certain examples, HR/MV is measured for a subject and tachyarrhythmia is indicated when HR/MV increases by an order of magnitude. In certain examples, the specified tachyarrhythmia detection threshold HR/MV value is a programmed value that is preferred by a physician or caregiver. In certain examples, the specified tachyarrhythmia detection threshold HR/MV value is determined based on a patient population.

In certain examples, cardiac depolarization interval can be used instead of heart rate in determining the ratio. In this case, the ratio calculated by the tachyarrhythmia detection circuit 820 would be:

$$\frac{60{,}000}{\text{Interval(ms)}} \times \frac{1}{MV}.$$

In certain examples, the respiration parameter includes tidal volume and the tachyarrhythmia detection circuit 820 calculates a ratio of HR/TV. In certain examples, the respiration parameter includes respiration rate and the tachyarrhythmia detection circuit 820 calculates a ratio of HR/RR.

According to some examples, the tachyarrhythmia detection circuit 820 continuously calculates the ratio to detect tachyarrhythmia. In certain examples, the tachyarrhythmia detection circuit 820 calculates the ratio periodically according to a specified (e.g., programmed) schedule. In certain examples, the tachyarrhythmia detection circuit 820 initiates calculation of the ratio in response to a detected physiologic event.

Such a detected physiologic event can include a detected heart rate. The tachyarrhythmia detection circuit 820 may compare a determined heart rate to a specified lowest tachyarrhythmia rate (LTR) detection threshold value, and calculate the ratio when the determined heart rate satisfies the specified LTR detection threshold. The LTR detection threshold value may be heart rate or depolarization interval determined for a patient population, or may be a detection threshold rate value or detection interval value that is preferred by a physician.

In some examples, the device 800 includes a memory circuit 835 integral to, or communicatively coupled to, the control circuit 815. The tachyarrhythmia detection circuit 820 compares the determined heart rate to a specified lowest tachyarrhythmia rate (LTR) detection threshold value, and generates an indication of slow tachyarrhythmia when the heart rate is less than the specified LTR detection threshold value and the calculated ratio satisfies a specified detection ratio threshold value. The tachyarrhythmia detection circuit 820 may store the indication of slow tachyarrhythmia using the memory circuit 835.

In some examples, the calculated ratio must satisfy the tachyarrhythmia detection threshold value for a specified minimum period of time before the tachyarrhythmia detection circuit 820 generates the indication of tachyarrhythmia. In certain examples, the tachyarrhythmia detection circuit 820 generates an indication of tachyarrhythmia when the determined heart rate and the calculated ratio satisfy the LTR detection threshold and the specified detection ratio threshold, respectively, for a specified minimum detection time duration threshold value.

In some examples, the detected physiologic event can include activity of the subject. The device 800 may include an activity sensing circuit (e.g., an accelerometer) communicatively coupled to the control circuit that provides a signal representative of subject activity. The tachyarrhythmia detection circuit 820 calculates the ratio when detecting that the determined heart rate satisfies the specified LTR detection threshold value. As described previously, the tachyarrhythmia detection circuit 820 generates an indication of tachyarrhythmia when the calculated ratio satisfies the specified tachyarrhythmia detection ratio threshold value. The tachyarrhythmia detection circuit 820 may also generate an indication of activity-induced tachyarrhythmia when the specified tachyarrhythmia detection ratio threshold value is not satisfied and an activity level indicated by the activity signal exceeds an activity level threshold value.

When the calculated ratio satisfies the specified detection ratio threshold value, the tachyarrhythmia detection circuit 820 provides the indication of tachyarrhythmia to a user or process. In some examples, the device 800 includes a display (e.g., if the device 800 is wearable) and the indication of tachyarrhythmia is presented to the user on the display. The calculated ratio can also be provided on the display.

In some examples, a second separate device communicates with the ambulatory medical device 800 and the second device includes a display. In certain examples, the medical device 800 and the second device include wireless interfaces and the communication is wireless such as by near field inductive telemetry, or by far-field radio frequency (RF) communication. In certain examples, the devices include wired interfaces (e.g., a wearable ambulatory medical device with a serial (e.g., USB) port).

According to some examples, the device 800 includes a therapy circuit 830 communicatively coupled to the control circuit and selectively delivers electrical cardioversion/defibrillation shock therapy and electrical pacing stimulation energy to the heart. When the heart rate exceeds the LTR threshold, the control circuit 815 may initiate delivery of cardioversion/defibrillation shock therapy in response to the generated indication of tachyarrhythmia when the calculated ratio satisfies the tachyarrhythmia detection ratio threshold value. If the heart rate exceeds the LTR threshold but the calculated ratio does not satisfy the tachyarrhythmia detection ratio threshold value, the control circuit 815 may initiate delivery of anti-tachyarrhythmia pacing (ATP) therapy in response to the indication of tachyarrhythmia.

By monitoring heart rate and respiration, the tachyarrhythmia detection circuit 820 can provide improved sensitivity to the hemodynamic status of the subject. This could reduce unnecessary shocks for episodes of VT and SVT that are tolerable to the subject.

Additional Notes

Example 1 includes subject matter (such as an implantable or other ambulatory medical apparatus comprising a cardiac signal sensing circuit configured to provide a sensed cardiac depolarization signal of a heart of a subject, a respiration sensing circuit configured to provide a signal representative of respiration of the subject, and a control circuit communicatively coupled to the cardiac signal sensing circuit and the respiration circuit. The control circuit includes a tachyarrhythmia detection circuit configured to determine heart rate using the depolarization signal, determine a respiration parameter of the subject using the respiration signal, calculate a ratio using the determined heart rate and the determined respiration parameter, generate an indication of tachyarrhythmia when the calculated ratio satisfies a specified tachyarrhythmia detection ratio threshold value, and provide the indication of tachyarrhythmia to a user or process.

In Example 2, the tachyarrhythmia detection circuit of Example 1 can optionally include a minute ventilation (MV) circuit configured to determine MV from the respiration signal as the respiration parameter, and the tachyarrhythmia detection circuit can optionally be configured to calculate the ratio using the determined heart rate and the determined MV.

In Example 3, the tachyarrhythmia detection circuit of one or any combination of Examples 1 and 2 can optionally be configured to compare the determined heart rate to a specified lowest tachyarrhythmia rate (LTR) detection threshold value, and calculate the ratio when the determined heart rate satisfies the specified LTR detection threshold.

In Example 4, the subject matter of one or any combination of Examples 1-3 can optionally include a therapy circuit communicatively coupled to the control circuit and configured to selectively deliver electrical cardioversion/defibrillation shock therapy and electrical pacing stimulation energy to the heart. The control circuit is can optionally be configured to initiate delivery of cardioversion/defibrillation shock therapy in response to the indication of tachyarrhythmia when the calculated ratio satisfies the tachyarrhythmia detection ratio threshold value, and initiate delivery of anti-tachyarrhythmia pacing (ATP) therapy in response to the indication of tachyarrhythmia otherwise.

In Example 5, the tachyarrhythmia detection circuit of one or any combination of Examples 1-4 can optionally be configured to generate an indication of tachyarrhythmia when the determined heart rate and the calculated ratio satisfy the LTR detection threshold and the specified detection ratio threshold, respectively, for a specified minimum detection time duration threshold value.

In Example 6, the MV circuit of one or any combination of Examples 2-5 can optionally be configured to extract respiration rate from the respiration signal, determine tidal volume using the respiration signal, and calculate MV of the subject using the respiration rate and tidal volume.

In Example 7, the subject matter of one or any combination of Examples 1-6 can optionally include a memory circuit integral to, or communicatively coupled to, the control circuit. The tachyarrhythmia detection circuit can optionally be configured to compare the determined heart rate to a specified lowest tachyarrhythmia rate (LTR) detection threshold value, generate an indication of slow tachyarrhythmia when the heart rate is less than the specified LTR detection threshold value and the calculated ratio satisfies a specified detection ratio threshold value, and store the indication of slow tachyarrhythmia using the memory circuit.

In Example 8, the subject matter of one or any combination of Examples 1-7 can optionally include an activity sensing circuit configured to provide a signal representative of activity of the subject. The tachyarrhythmia detection circuit can optionally be configured to detect that the determined heart rate satisfies a specified LTR detection threshold value, generate an indication of tachyarrhythmia when the calculated ratio satisfies the specified detection ratio threshold value, and generate an indication of activity-induced tachyarrhythmia when the specified detection ratio threshold value is not satisfied and an activity level indicated by the activity signal exceeds an activity level threshold value.

In Example 9, the respiration sensing circuit of one or any combination of Examples 1-8 can optionally include an intrathoracic impedance sensing circuit configured to provide an impedance signal representative of respiration of the subject.

In Example 10, the respiration circuit of one or any combination of Examples 1-9 can optionally include an accelerometer, and the respiration signal can optionally include an acceleration signal representative of motion of the thorax region of the subject.

Example 11 can include subject matter, or can optionally be combined with the subject matter of one or any combination of Examples 1-10 to include subject matter (such as a method, a means for performing acts, or a machine-readable medium including instructions that, when performed by the machine, cause the machine to perform acts) comprising determining heart rate of a subject, determining a respiration parameter of the subject, calculating a ratio using the determined heart rate and the determined respiration parameter, and generating an indication of tachyarrhythmia when the calculated ratio satisfies a specified detection ratio threshold value and providing the indication of the tachyarrhythmia to a user or process.

Such subject matter can include a means for determining heart rate of a subject, illustrative examples of which can include a cardiac signal sensing circuit and a control circuit having a tachyarrhythmia detection circuit. Such subject matter can include a means for determining a respiration parameter of the subject, illustrative examples of which can include a respiration sensing circuit, a transthoracic impedance circuit, an accelerometer, and a control circuit having a tachyarrhythmia detection circuit. Such subject matter can include a means for calculating a ratio using the determined heart rate and the determined respiration parameter, an illustrative example of which can include a control circuit having a tachyarrhythmia detection circuit. Such subject matter can include a means for generating an indication of tachyarrhythmia, an illustrative example of which can include a control circuit having a tachyarrhythmia detection circuit.

In Example 12, the determining the respiration parameter of Example 11 can optionally include determining MV for the subject.

In Example 13, the subject matter of one or any combination of Examples 11 and 12 can optionally include determining that the heart rate satisfies a specified lowest tachyarrhythmia rate (LTR) detection threshold value. The calculating the ratio can optionally include calculating the ratio when the heart rate satisfies the specified LTR detection threshold.

In Example 14, the subject matter of one or any combination of Examples 11-13 can optionally include initiating delivery of cardioversion/defibrillation shock therapy with the device when the calculated ratio satisfies the tachyarrhythmia detection ratio threshold value, and initiating delivery of anti-tachyarrhythmia pacing (ATP) therapy otherwise.

In Example 15, the generating an indication of tachyarrhythmia of one or any combination of Examples 1-14 can optionally include generating an indication of tachyarrhythmia when the determined heart rate and the calculated ratio satisfy the LTR detection threshold and the specified detection ratio threshold, respectively, for a specified minimum detection time duration threshold value.

In Example 16, the subject matter of one or any combination of Examples 11-15 can optionally include determining that the heart rate is less than a specified lowest tachyarrhythmia rate (LTR) detection threshold value, and generating an indication of slow tachyarrhythmia when the heart rate is less than the specified LTR detection threshold value and the calculated ratio satisfies a specified detection ratio threshold value.

In Example 17, subject matter of one or any combination of Examples 11-16 can optionally include monitoring activity of the subject, detecting an episode of tachyarrhythmia during a period of subject activity, generating an indication of tachyarrhythmia for the episode when the calculated ratio satisfies the specified detection ratio threshold value, and generating an indication of activity-induced tachyarrhythmia for the episode otherwise.

In Example 18, the determining MV of one or any combination of Examples 12-17 can optionally include sensing a physiologic signal representative of respiration using the device, extracting respiration rate from the physiologic signal representative of respiration, determining tidal volume using the physiologic signal representative of respiration, and calculating MV of the subject using the respiration rate and tidal volume.

In Example 19, the sensing a physiologic signal representative of respiration of one or any combination of Examples 11-18 can optionally include sensing an intra-thoracic impedance signal using the device.

In Example 20, the sensing a physiologic signal representative of respiration of one or any combination of Examples 11-19 can optionally include sensing motion of the thorax region of the subject using an accelerometer.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks; random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An implantable or other ambulatory medical apparatus comprising:
   a cardiac signal sensing circuit configured to provide a sensed cardiac depolarization signal of a heart of a subject;
   a respiration sensing circuit configured to provide a signal representative of respiration of the subject; and
   a control circuit communicatively coupled to the cardiac signal sensing circuit and the respiration circuit, wherein the control circuit includes a tachyarrhythmia detection circuit configured to:

determine heart rate using the depolarization signal;
determine a respiration parameter of the subject using the respiration signal;
calculate a ratio of the determined heart rate and the determined respiration parameter and determine a normal baseline value of the ratio;
generate an indication of tachyarrhythmia when the calculated ratio satisfies a ventricular tachycardia ratio detection zone, wherein a value of the calculated ratio of the ventricular tachycardia detection zone is a substantial increase over the normal baseline value of the ratio; and
provide the indication of tachyarrhythmia to a user or process.

2. The apparatus of claim 1,
wherein the tachyarrhythmia detection circuit includes a minute ventilation (MV) circuit configured to determine MV from the respiration signal as the respiration parameter, and
wherein the tachyarrhythmia detection circuit is configured to calculate the ratio using the determined heart rate and the determined MV.

3. The apparatus of claim 2, wherein the tachyarrhythmia detection circuit is configured to:
compare the determined heart rate to a specified lowest tachyarrhythmia rate (LTR) detection threshold value, and
calculate the ratio when the determined heart rate satisfies the specified LTR detection threshold.

4. The apparatus of claim 3, including:
a therapy circuit communicatively coupled to the control circuit and configured to selectively deliver electrical cardioversion/defibrillation shock therapy and electrical pacing stimulation energy to the heart;
wherein the control circuit is configured to:
initiate delivery of cardioversion/defibrillation shock therapy in response to the indication of tachyarrhythmia when the calculated ratio satisfies the ventricular tachycardia ratio detection zone; and
initiate delivery of anti-tachyarrhythmia pacing (ATP) therapy in response to the indication of tachyarrhythmia otherwise.

5. The apparatus of claim 3, wherein the tachyarrhythmia detection circuit is configured to generate an indication of tachyarrhythmia when the determined heart rate and the calculated ratio satisfy the LTR detection threshold and the specified ventricular tachycardia ratio detection zone, respectively, for a specified minimum detection time duration threshold value.

6. The apparatus of claim 2, wherein the MV circuit is configured to:
extract respiration rate from the respiration signal;
determine tidal volume using the respiration signal; and
calculate MV of the subject using the respiration rate and tidal volume.

7. The apparatus of claim 2, including:
a memory circuit integral to, or communicatively coupled to, the control circuit,
wherein the tachyarrhythmia detection circuit is configured to:
compare the determined heart rate to a specified lowest tachyarrhythmia rate (LTR) detection threshold value;
generate an indication of slow tachyarrhythmia when the heart rate is less than the specified LTR detection threshold value and the calculated ratio satisfies a specified ventricular tachycardia ratio detection zone value; and
store the indication of slow tachyarrhythmia using the memory circuit.

8. The apparatus of claim 1, including:
an activity sensing circuit configured to provide a signal representative of activity of the subject;
wherein the tachyarrhythmia detection circuit is configured to:
detect that the determined heart rate satisfies a specified lowest tachyarrhythmia rate (LTR) detection threshold value;
generate an indication of tachyarrhythmia when the calculated ratio satisfies the specified ventricular tachycardia ratio detection zone value; and
generate an indication of activity-induced tachyarrhythmia when the specified detection ratio threshold value is not satisfied and an activity level indicated by the activity signal exceeds an activity level threshold value.

9. The apparatus of claim 1, wherein the respiration sensing circuit includes an intra-thoracic impedance sensing circuit configured to provide an impedance signal representative of respiration of the subject.

10. The apparatus of claim 1, wherein the respiration sensing circuit includes an accelerometer, and wherein respiration signal includes an acceleration signal representative of motion of the thorax region of the subject.

11. The apparatus of claim 1, wherein the value of the calculated ratio of the ventricular tachycardia detection zone is an order of magnitude increase over the normal baseline value of the ratio.

* * * * *